(12) United States Patent
Vera-Gonzalez et al.

(10) Patent No.: US 11,615,508 B2
(45) Date of Patent: Mar. 28, 2023

(54) SYSTEMS AND METHODS FOR CONSISTENT PRESENTATION OF MEDICAL IMAGES USING DEEP NEURAL NETWORKS

(71) Applicant: GE Precision Healthcare LLC, Milwaukee, WI (US)

(72) Inventors: German Guillermo Vera-Gonzalez, Menomonee Falls, WI (US); Najib Akram, Waukesha, WI (US); Ping Xue, Pewaukee, WI (US); Fengchao Zhang, Hartland, WI (US); Gireesha Chinthamani Rao, Pewaukee, WI (US); Justin Wanek, Madison, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 369 days.

(21) Appl. No.: 16/785,283

(22) Filed: Feb. 7, 2020

(65) Prior Publication Data

US 2021/0248716 A1 Aug. 12, 2021

(51) Int. Cl.
*G06T 3/00* (2006.01)
*G06T 3/40* (2006.01)
(Continued)

(52) U.S. Cl.
CPC .......... *G06T 3/4046* (2013.01); *G06F 3/0481* (2013.01); *G06F 3/04847* (2013.01);
(Continued)

(58) Field of Classification Search
CPC .................. G06T 3/4046; G06T 7/174; G06T 2207/10072; G06T 2207/10116; G06T 2207/20081; G06T 2207/20084; G06T 2207/20092; G06T 2207/30004; G06T 1/20; G06T 5/008; G06T 7/0012; G06T 11/008; G06T 2207/30008; G06F 3/0481; G06F 3/04847; G06F 16/51; G06F 3/04845; G06K 9/6256; G06K 9/6267; G06K 9/6253; G06K 9/6271; G06N 3/04;
(Continued)

(56) References Cited

U.S. PATENT DOCUMENTS

2011/0251980 A1* 10/2011 Kapoor .................. G06N 20/00
713/100
2020/0202524 A1* 6/2020 Karki ...................... G06T 5/008

OTHER PUBLICATIONS

"Digital Radiography—Intelligent imaging," Context Vision Website, Available Online at https://media.contextvision.com/2019/06/CoV-DR.pdf, Available as Early as Jan. 2019, 8 pages.

* cited by examiner

*Primary Examiner* — Nancy Bitar
*Assistant Examiner* — Xiao Liu

(57) ABSTRACT

A method for automatic selection of display settings for a medical image is provided. The method includes receiving a medical image, mapping the medical image to an appearance classification cell of an appearance classification matrix using a trained deep neural network, selecting a first WW and a first WC for the medical image based on the appearance classification and a target appearance classification, adjusting the first WW and the first WC based on user preferences to produce a second WW and a second WC, and displaying the medical image with the second WW and the second WC via a display device.

10 Claims, 9 Drawing Sheets

(51) Int. Cl.
  *G06F 3/04847* (2022.01)
  *G06F 3/0481* (2022.01)
  *G06K 9/62* (2022.01)
  *G06N 3/04* (2023.01)
  *G16H 30/40* (2018.01)
  *G16H 30/20* (2018.01)
  *G06F 16/51* (2019.01)
  *G06N 3/08* (2023.01)
  *G06T 7/174* (2017.01)
  *G06N 20/00* (2019.01)

(52) U.S. Cl.
  CPC ............ *G06F 16/51* (2019.01); *G06K 9/6256* (2013.01); *G06K 9/6267* (2013.01); *G06N 3/04* (2013.01); *G06N 3/08* (2013.01); *G06N 20/00* (2019.01); *G06T 7/174* (2017.01); *G16H 30/20* (2018.01); *G16H 30/40* (2018.01)

(58) Field of Classification Search
  CPC ........ G06N 3/08; G06N 20/00; G06N 3/0454; G06N 3/084; G16H 30/20; G16H 30/40; G16H 50/20; G16H 50/70; G06V 10/82; G06V 2201/033
  See application file for complete search history.

SYSTEMS AND METHODS FOR CONSISTENT PRESENTATION OF MEDICAL IMAGES USING DEEP NEURAL NETWORKS

TECHNICAL FIELD

Embodiments of the subject matter disclosed herein relate to medical imaging, and more particularly, to systems and methods for determining display settings for medical images using deep neural networks.

BACKGROUND

Medical imaging devices are often used to obtain internal physiological information of a patient. For example, a medical imaging device may be used to obtain images of the bone structure, the brain, the heart, the lungs, and various other anatomical regions of a patient. Medical imaging devices may include magnetic resonance imaging (MRI) systems, computed tomography (CT) systems, positron emission tomography (PET) systems, PET/MR systems, x-ray systems, ultrasound systems, C-arm systems, and various other imaging modalities.

A clinician may evaluate a patient's condition based on the physiological information captured in a medical image by a medical imaging device. Accurate and consistent evaluation of medical images by a clinician is, in part, reliant on consistent display appearance of medical images. Display appearance, also referred to herein as presentation, is a function of the display settings for the medical images, such as window-width (WW) and window-center (WC), which are related to the contrast and brightness of a displayed medical image, respectively. One complaint received from radiologists is the lack of display appearance consistency in medical images from different patients, from the same patient acquired at different times, or from the same patient acquired using different imaging devices. Inconsistent presentation of medical images complicates the image review workflow, as clinicians may need to manually adjust the display settings of a medical image to achieve a desired look.

In image processing algorithms, which may be used to automatically set display settings, a significant portion of the inconsistency in presentation comes from the histogram analysis of the image, as metal objects, edge detection failures, raw radiation mask failures, field of view changes, and incorrect exam selection, may skew the histogram analysis and result in display settings which produce a medical image having a display appearance substantially different from the desired look of the user, and which may vary from image to image based on the presence of noise or other artifacts. Further, histogram analysis does not incorporate contextual information for the pixel intensity data of medical images, e.g., histogram analysis is blind regarding which pixels of a medical image correspond to regions of anatomy, and which pixels correspond to background, noise, or artifacts, and therefor histogram analysis is unable to selectively adjust display settings based on display appearance of anatomical regions of interest.

Therefore, it is generally desirable to explore techniques for intelligently selecting display settings for medical images to produce medical images having consistent display appearance.

SUMMARY

The current disclosure enables more consistent presentation of medical images, using deep neural networks. In a first embodiment, the current disclosure provides a method comprising, receiving a medical image, mapping the medical image to an appearance classification cell of an appearance classification matrix using a trained deep neural network, selecting a first WW and a first WC for the medical image based on the appearance classification and a target appearance classification, adjusting the first WW and the first WC based on user preferences to produce a second WW and a second WC, and displaying the medical image with the second WW and the second WC via a display device. By mapping the medical image to the appearance classification cell of the appearance classification matrix using the trained deep neural network, a more holistic assessment of the appearance of the medical image may be made. Said assessment, which comprises a learned mapping from features of the medical image to one or more pre-determined classes (appearance classification cells), may more closely match a human's assessment of medical image presentation display appearance. Further, the trained deep neural network may incorporate contextual information for the medical image data, by classifying medical images based on the spatial configuration and types of features present, as opposed to evaluating medical images based on pixel intensity histograms alone.

The learned mapping may also be substantially less sensitive to noise and/or image artifacts than conventional histogram analysis, as the trained deep neural network may differentiate between regions of a medical image comprising noise or image artifacts, and regions of the medical image comprising anatomical regions of interest. Thus, the appearance classification cell output by the deep neural network may be more heavily based on appearance characteristics of anatomical regions of interest, and less heavily based on appearance characteristics of background/noise/artifacts.

Further, the appearance classification cell of the appearance classification matrix may comprise an indication of a WW difference between the appearance classification cell and the target appearance classification, as well as a WC difference between the appearance classification cell and the target appearance classification cell, thus enabling the first WW and the first WC to be selected based on said WW difference and said WC difference, wherein an appearance of the medical image displayed with the first WW and the first WC may match the target appearance classification.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

Figure 1:
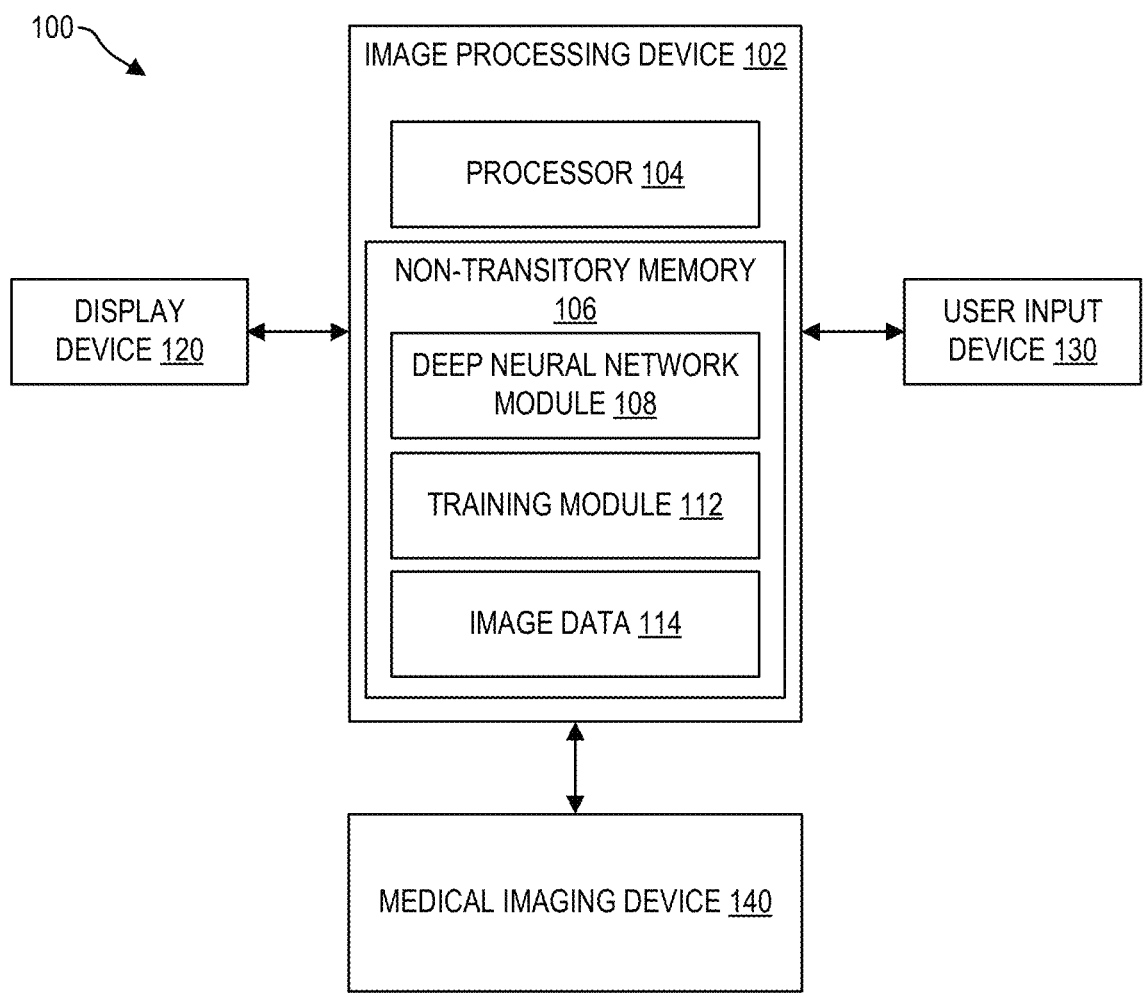
FIG. 1 shows a block diagram of an exemplary embodiment of a medical imaging system.

The drawings illustrate specific aspects of the described systems and methods for consistent presentation of medical images using deep neural networks. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

The following description relates to systems and methods for intelligently selecting display settings for medical images using deep neural networks, to produce medical images having consistent display appearance, thereby enabling more consistent and accurate evaluation and comparison of medical images. Current approaches for automatically selecting display settings for medical images rely on histogram analysis, which is sensitive to the presence of noise and/or artifacts in the medical image being evaluated, and which may produce medical images having inconsistent display appearance.

The inventors herein have identified approaches that may enable automatic selection of display settings which, when applied to medical images, may produce more consistent display appearance. Further, the approaches of selecting display settings herein disclosed possess decreased sensitivity to noise and/or artifacts in the medical images being evaluated. The current disclosure also provides systems and methods for training deep neural networks using training data pairs to learn a map from medical image features to appearance classification cells of an appearance classification matrix. Methods and systems are also herein disclosed for generating said training data pairs.

Figure 8:
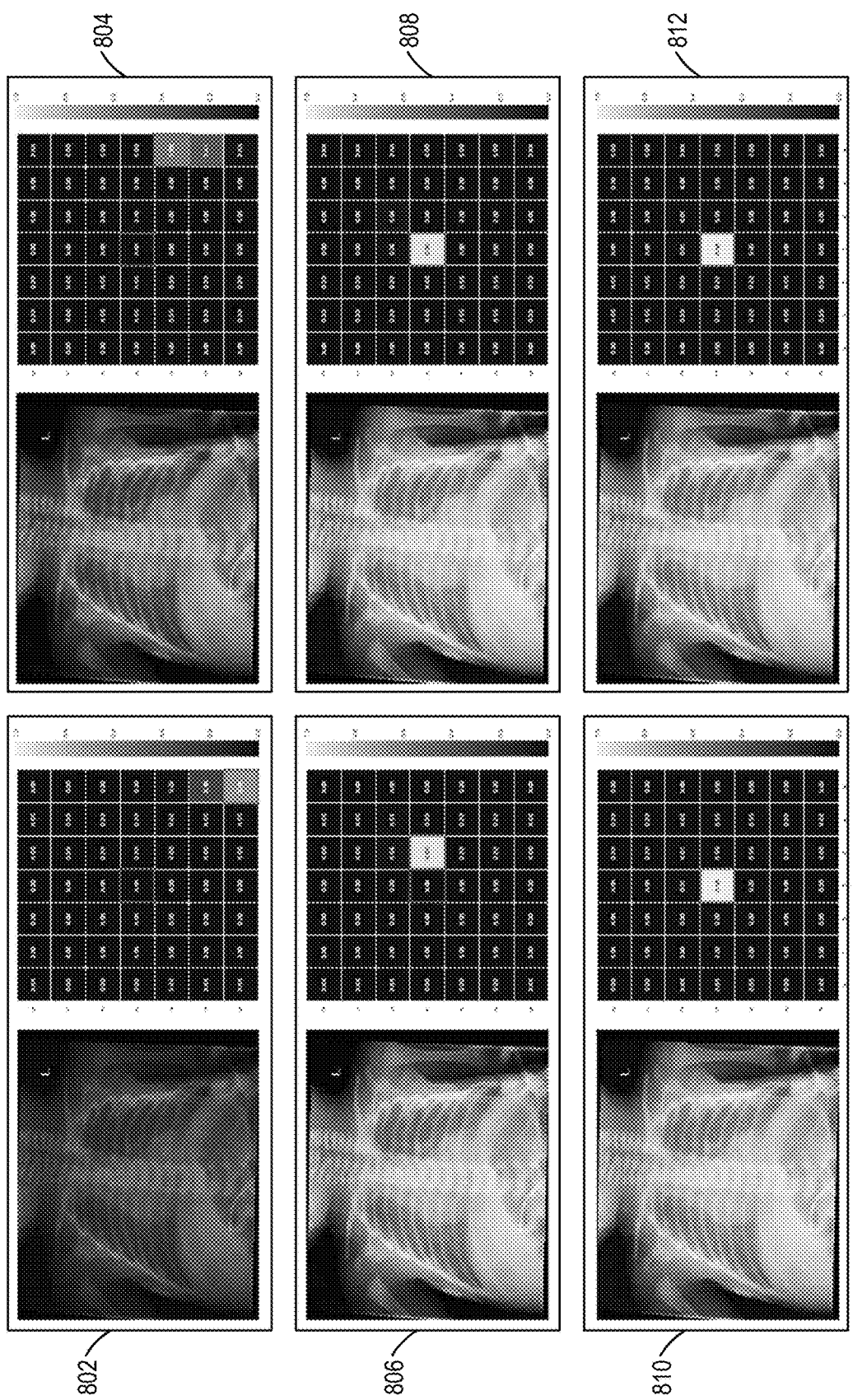
FIG. 8 illustrates an example of iteratively selecting display settings for a medical image to match a target appearance classification.
Figure 9:
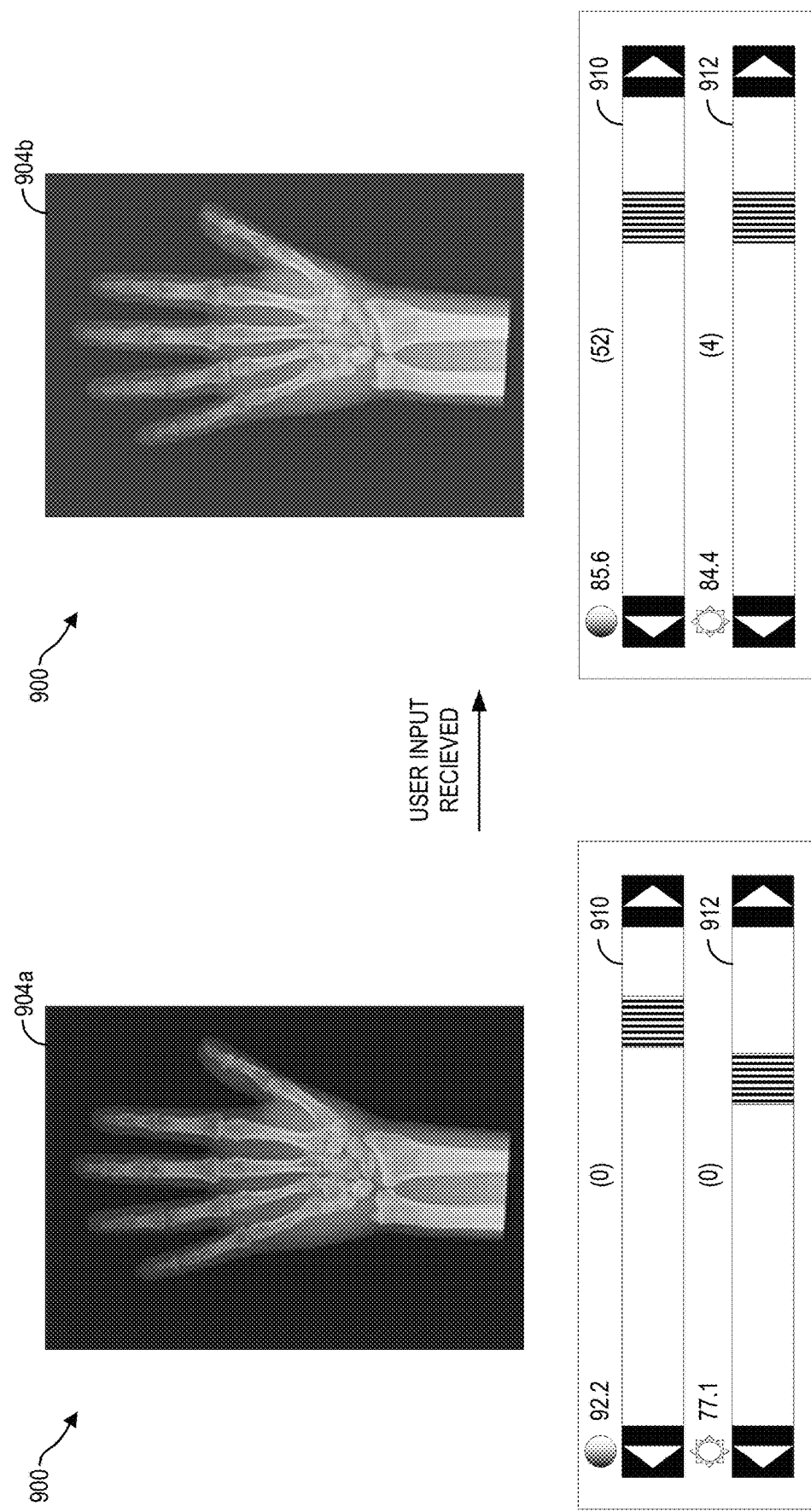
FIG. 9 shows an example of a graphical user interface by which a user may adjust display settings of a medical image.

In one embodiment, the current disclosure provides a medical imaging system 100, shown in FIG. 1, configured to acquire medical images using a medical imaging device 140. The medical imaging system 100 further comprises an image processing device 102, which may include one or more trained deep neural networks. The image processing device 102 may further comprise instructions for selecting display settings of one or more medical images based on an appearance classification cell output by a trained deep neural network, by executing one or more operations of method 200, shown in FIG. 2. In some embodiments, method 200 includes iteratively updating display settings of a medical image, until the appearance classification cell output by the trained deep neural network for the medical image matches a pre-determined target appearance classification, as illustrated in FIG. 8. Method 200 may further include receiving user input, via a graphical user interface, such as graphical user interface 900, shown in FIG. 9, and further adjusting the display settings based on said user input, as illustrated in FIG. 9.

Method 200 may enable automatic selection of display settings for each of a plurality of medical images, such that the display appearance of each of the plurality of medical images is brought into uniformity with a user's preferred display appearance (a process herein referred to as appearance normalization). Increased consistency in medical image presentation may enable a clinician to more easily evaluate or diagnose medical images, as the overall display appearance of the medical images may be brought into uniformity with a clinician's preferences. Further, consistency in medical image presentation may enable more easier and more accurate comparison between distinct medical images (e.g., determining an amount of tumor growth between a first medical image and a second medical image).

Figure 6:
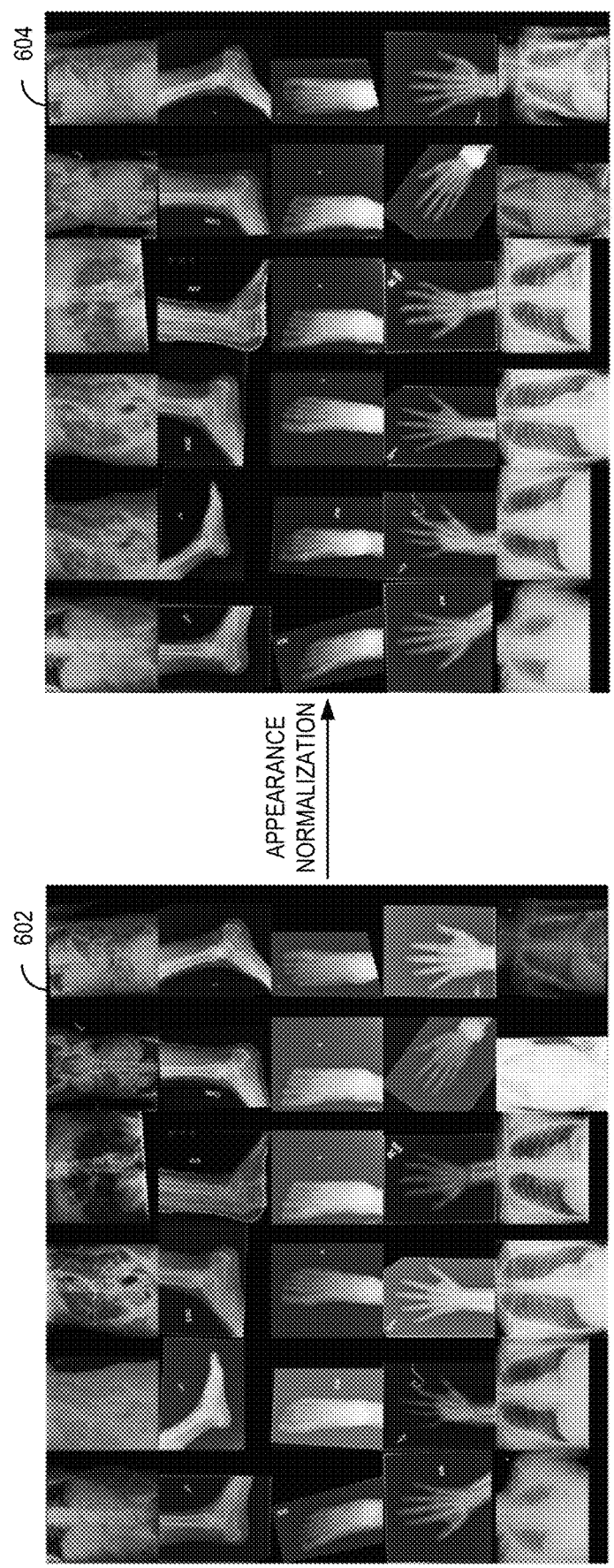
FIG. 6 shows a comparison between a plurality of medical images with display settings selected using a conventional approach, and the same plurality of medical images with display settings selected using the approach of the current disclosure.
Figure 7:
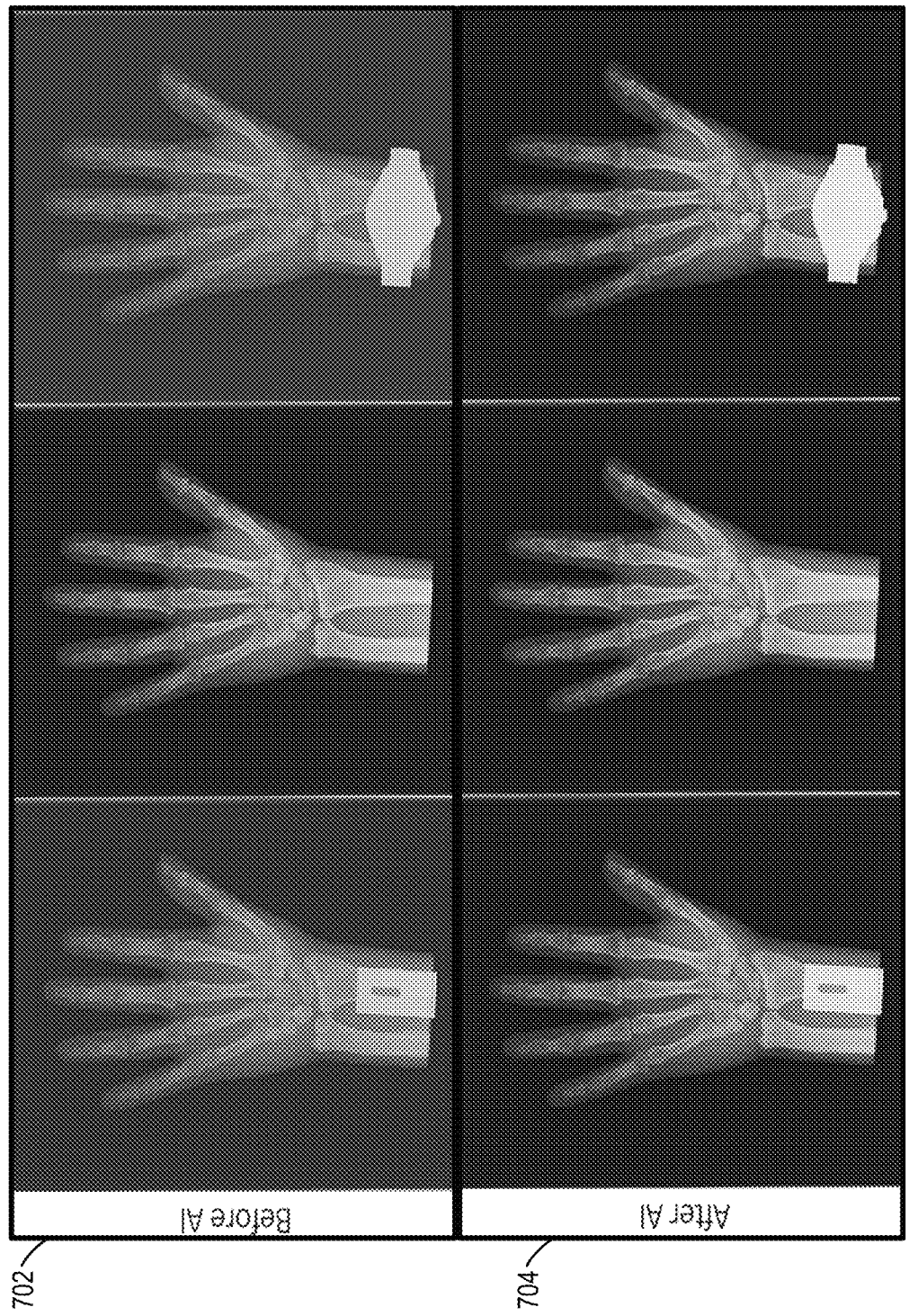
FIG. 7 shows a comparison between medical images with display settings selected according to a conventional approach, and the same medical images with display settings selected using the approach of the current disclosure.

FIG. 6 and FIG. 7 provide comparisons of medical images having display settings selected using conventional approaches (first plurality of medical images 602 and first plurality of hand images 702), and medical images having display settings selected according to approaches of the current disclosure (second plurality of medical images 604 and second plurality of hand images 704).

Figure 3:
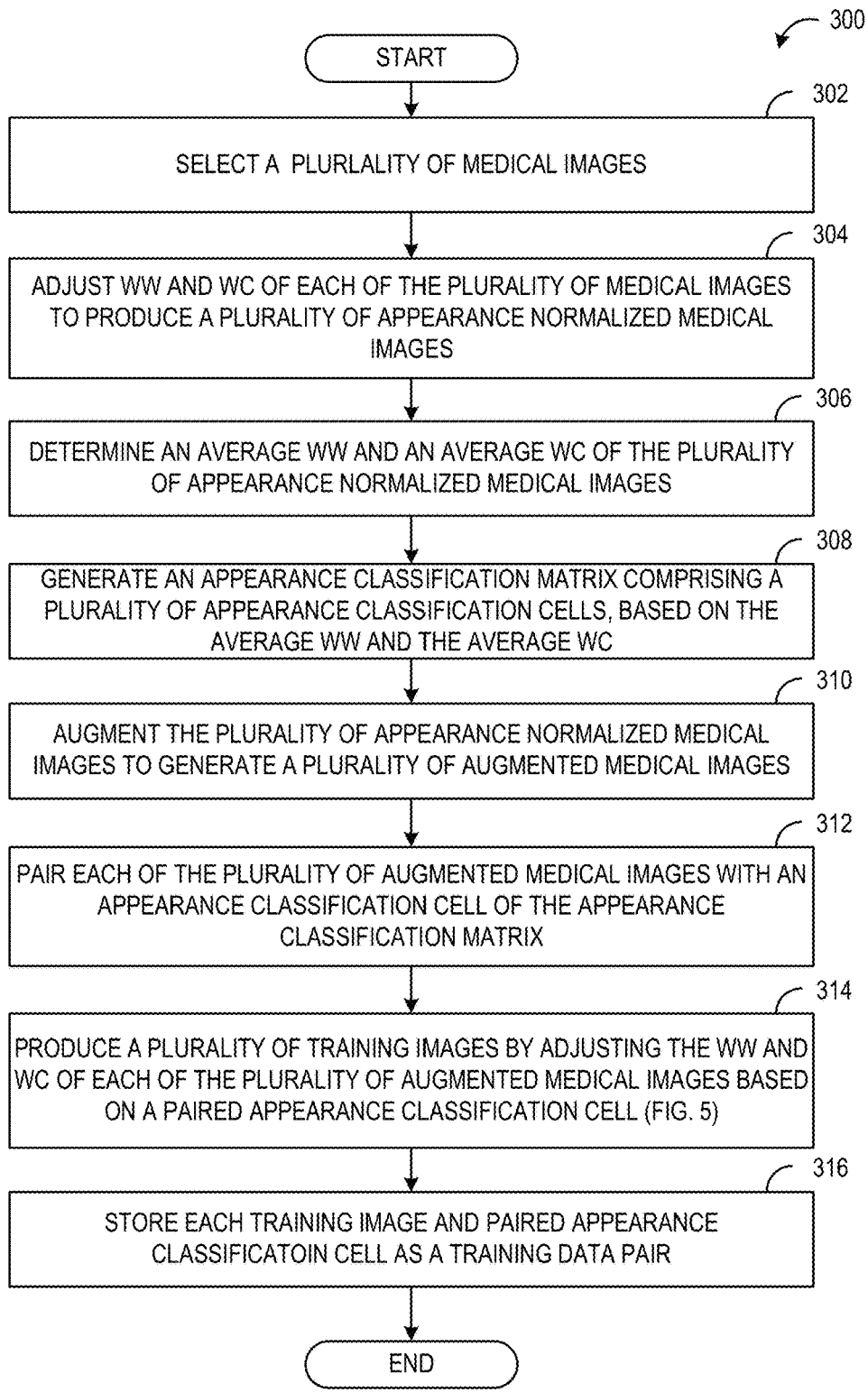
FIG. 3 shows a flowchart of an exemplary method for generating training data pairs for training a deep neural network to map medical images to one or more appearance classification cells of an appearance classification matrix.
Figure 5:
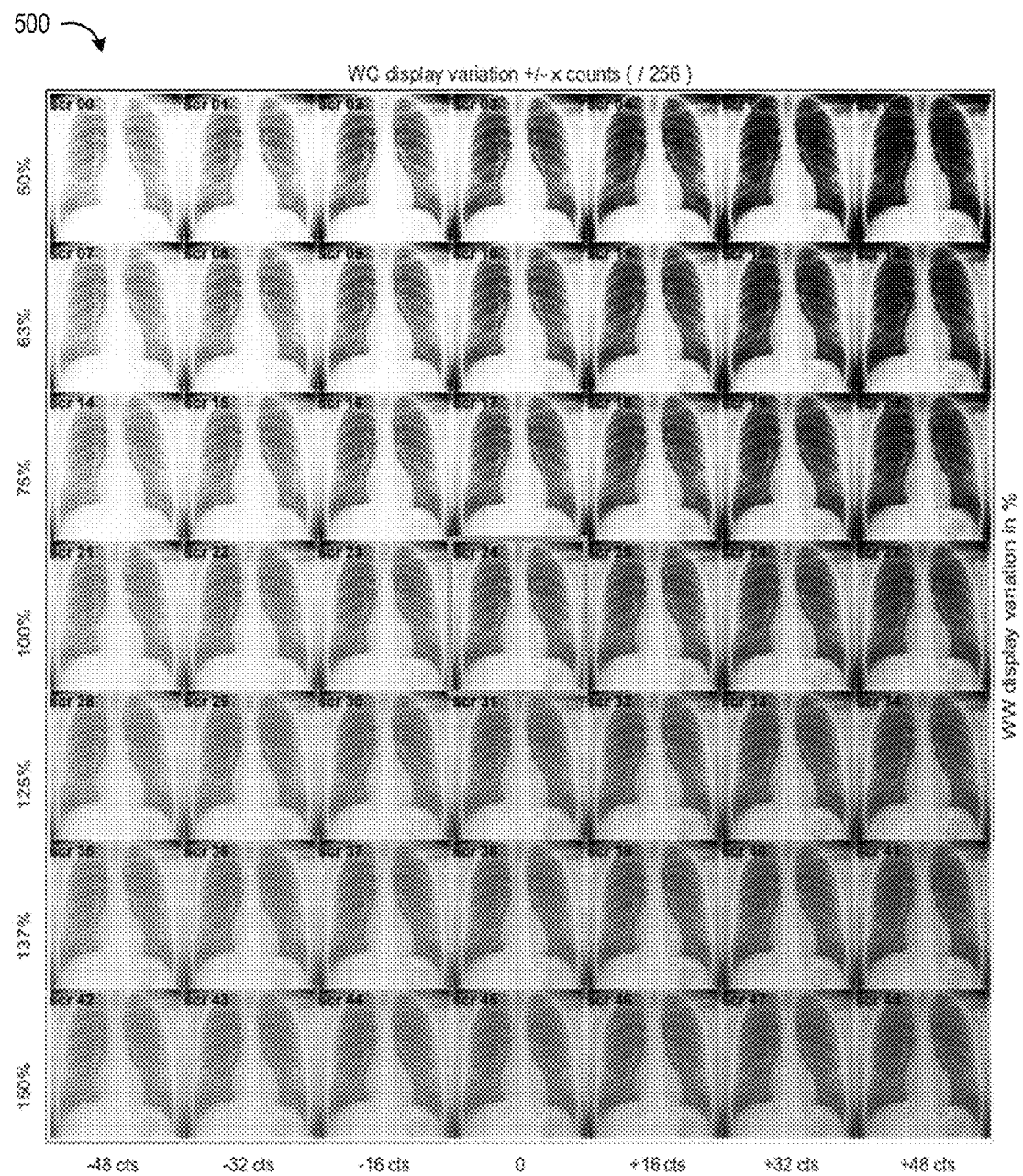
FIG. 5 shows an example of a plurality of training images generated according to an exemplary embodiment of the current disclosure.

The trained deep neural network, employed in method 200, may be trained to classify medical images into one or more appearance classification cells of an appearance classification matrix according to one or more operations of method 400, using training data pairs generated by execution of one or more operations of method 300, shown in FIG. 3. In some embodiments, the training data pairs may be generated by adjusting display settings, such as WW and WC, relative to average display settings of a target appearance classification, based on an assigned ground truth appearance classification cell. FIG. 5 shows an illustration of a plurality of training images 500, wherein each of the plurality of training images 500 is positioned based on a position of an assigned ground truth appearance classification cell within an appearance classification matrix. Each of the plurality of training images 500 possesses display settings corresponding to an assigned ground truth appearance classification cell, and thus plurality of training images 500 appear to represent a spectrum of brightness and contrast settings.

It will be appreciated that, although a majority of examples are given with respect to WW and WC, aspects of the current approach may be advantageously employed to select other display settings, including gamma (for gamma correction), value-of-interest (VOI) selection, etc., without departing from the scope of the current disclosure.

Referring to FIG. 1, a medical imaging system 100 is shown, in accordance with an exemplary embodiment. Medical imaging system 100 comprises image processing device 102, display device 120, user input device 130, and medical imaging device 140. In some embodiments, at least a portion of medical imaging system 100 is disposed at a remote device (e.g., edge device, server, etc.) communicably coupled to the medical imaging system 100 via wired and/or wireless connections. In some embodiments, at least a portion of image processing device 102 is disposed at a separate device (e.g., a workstation) configured to receive images from a storage device which stores images acquired by medical imaging device 140.

Image processing device 102 includes a processor 104 configured to execute machine readable instructions stored in non-transitory memory 106. Processor 104 may be single core or multi-core, and the programs executed thereon may be configured for parallel or distributed processing. In some embodiments, the processor 104 may optionally include individual components that are distributed throughout two or more devices, which may be remotely located and/or configured for coordinated processing. In some embodiments, one or more aspects of the processor 104 may be virtualized and executed by remotely-accessible networked computing devices configured in a cloud computing configuration.

Non-transitory memory 106 may store deep neural network module 108, training module 112, and image data 114. Deep neural network module 108 may include one or more deep neural networks, comprising a plurality of weights and biases, activation functions, and instructions for implementing the one or more deep neural networks to map medical images to appearance classification cell(s) of an appearance classification matrix. For example, deep neural network module 108 may store instructions for implementing one or more deep neural networks, according to one more steps of method 200, to map medical images to corresponding appearance classification cells, based on identified features in the medical images.

Deep neural network module 108 may include trained and/or un-trained deep neural networks. In some embodiments, the deep neural network module 108 is not disposed at the image processing device 102, but is disposed at a remote device communicably coupled with image processing device 102 via wired or wireless connection. Deep neural network module 108 may include various deep neural network metadata pertaining to the trained and/or un-trained networks. In some embodiments, the deep neural network metadata may include an indication of the training data used to train a deep neural network, a training method employed to train a deep neural network, and an accuracy/validation score of a trained deep neural network. In some embodiments, deep neural network module 108 may include metadata for a trained deep neural network indicating a type of anatomy, and/or a type of imaging modality, to which the trained deep neural network may be applied.

Non-transitory memory 106 further includes training module 112, which comprises machine executable instructions for training one or more of the deep neural networks stored in deep neural network module 108. In some embodiments, training module 112 may include instructions for generating training data pairs by executing one or more operations of method 300, and utilizing said training data pairs to train a deep neural network to classify medical images into one or more appearance classification cells of an appearance classification matrix by executing one or more operations of method 400 shown in FIG. 4. In one embodiment, the training module 112 may include gradient descent algorithms, loss functions, and rules for generating and/or selecting training data for use in training a deep neural network. Training module 112 may further include instructions, that when executed by processor 104, cause image processing device 102 to train a deep neural network by executing one or more of the operations of method 400, discussed in more detail below with reference to FIG. 4. In some embodiments, the training module 112 is not disposed at the image processing device 102, but is disposed remotely, and is communicably coupled with image processing device 102.

Non-transitory memory 106 may further store image data 114, comprising medical images/imaging data acquired by medical imaging device 140. Image data 114 may further comprise medical images/imaging data received from other medical imaging systems, via communicative coupling with the other medical imaging systems. The medical images stored in image data 114 may comprise medical images from various imaging modalities or from various models of medical imaging devices, and may comprise images of various views of anatomical regions of one or more patients. In some embodiments, medical images stored in image data 114 may include information identifying an imaging modality and/or an imaging device (e.g., model and manufacturer of an imaging device) by which the medical image was acquired. In some embodiments, image data 114 may comprise x-ray images acquired by an x-ray device, MR images captured by an MRI system, CT images captured by a CT imaging system, PET images captures by a PET system, and/or one or more additional types of medical images.

Medical images stored at image data 114 may further include display settings, which may be used by image processing device 102 in conjunction with display device 120 to display one or more medical images with a user preferred display appearance (e.g., brightness, contrast, etc.). In some embodiments, image data 114 stores look-up-tables (LUTs) associated with one or more medical images stored therein, for mapping base pixel intensity data of the one or more medical images to display intensity data. The LUTs may be generated based on display settings, which, in some embodiments, may be intelligently selected by execution of one or more steps of method 200, discussed in more detail below. In some embodiments, image data 114 may comprise pixel intensity histograms of one or more images stored therein.

In some embodiments, the non-transitory memory 106 may include components disposed at two or more devices, which may be remotely located and/or configured for coordinated processing. In some embodiments, one or more aspects of the non-transitory memory 106 may include remotely-accessible networked storage devices configured in a cloud computing configuration.

Medical imaging system 100 further includes medical imaging device 140, which may comprise substantially any type of medical imaging device, including x-ray, MRI, CT, PET, hybrid PET/MR, ultrasound, etc. Imaging device 140 may acquire measurement data of an anatomical region of a patient, which may be used to generate medical images. The medical images generated from measurement data acquired by medical imaging device 140 may comprise two-dimensional (2D) or three-dimensional (3D) imaging data, wherein said imaging data may comprise a plurality of pixel intensity values (in the case of 2D medical images) or voxel intensity values (in the case of 3D medical images). The medical images acquired by medical imaging device 140 may comprise gray scale, or color images, and therefore the medical images stored in image data 114 may comprise a single color channel for gray scale images, or a plurality of color channels for colored medical images.

Medical imaging system 100 may further include user input device 130. User input device 130 may comprise one or more of a touchscreen, a keyboard, a mouse, a trackpad, a motion sensing camera, or other device configured to enable a user to interact with and manipulate data within image processing device 102. In some embodiments, user input device 130 may enable a user to adjust brightness and contrast of a medical image, using a graphical user interface (GUI), such as GUI 900 shown in FIG. 9.

Display device 120 may include one or more display devices utilizing virtually any type of technology. In some embodiments, display device 120 may comprise a computer monitor configured to display medical images of various types and styles. Display device 120 may be combined with processor 104, non-transitory memory 106, and/or user input device 130 in a shared enclosure, or may be a peripheral display device and may comprise a monitor, touchscreen, projector, or other display device known in the art, which may enable a user to view medical images having display settings selected according to one or more embodiments of the current disclosure, and/or interact with various data stored in non-transitory memory 106.

It should be understood that medical imaging system 100 shown in FIG. 1 is for illustration, not for limitation. Another appropriate medical imaging system 100 may include more, fewer, or different components.

Figure 2:
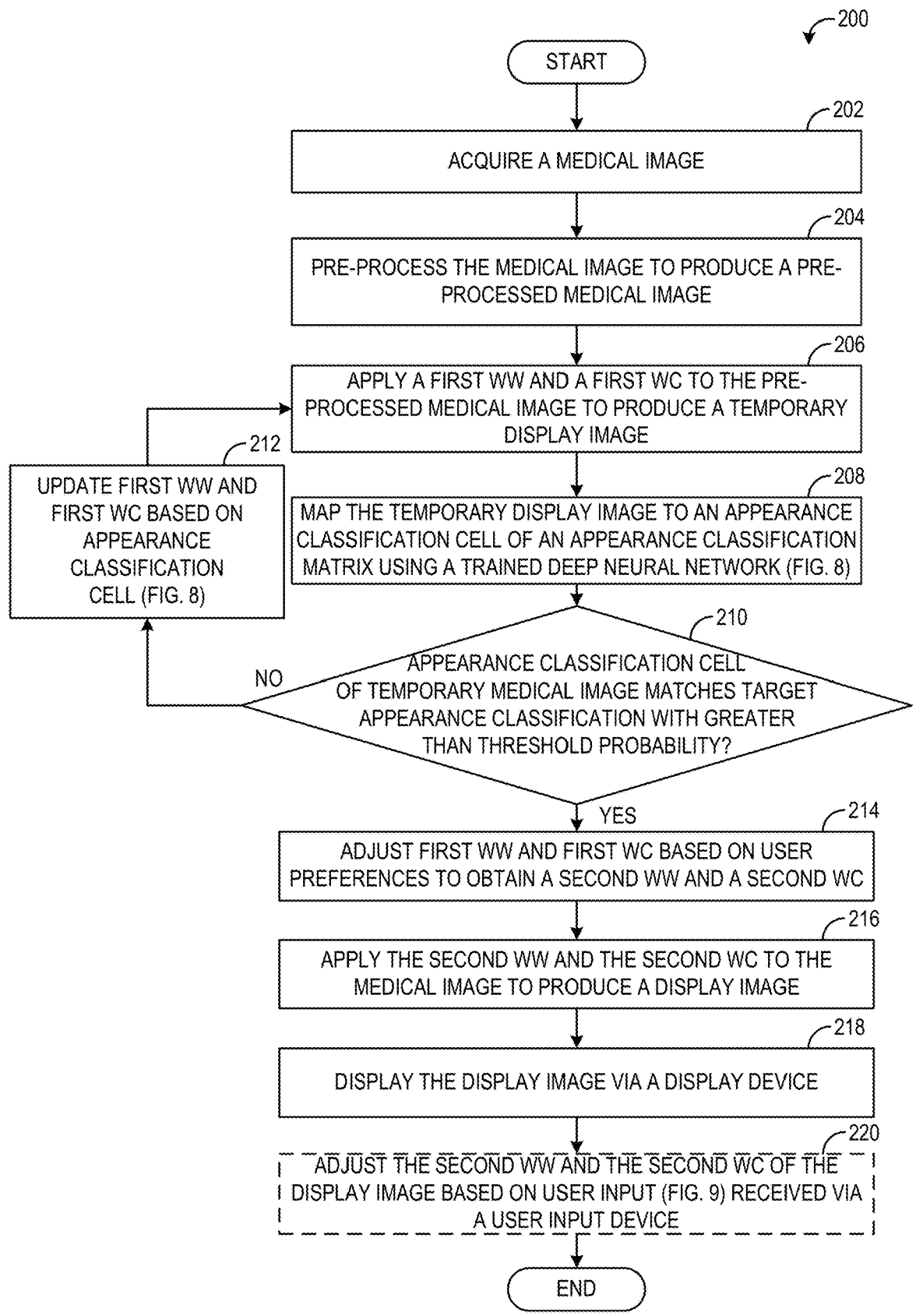
FIG. 2 shows a flowchart of an exemplary method for determining display settings for one or more medical images using a trained deep neural network.

Turning to FIG. 2, an example method 200 for intelligently selecting display settings for one or more medical images, based on output from a deep neural network, is shown. Method 200 may enable more consistent presentation of medical images by iteratively adjusting display settings for one or more medical images, until an appearance classification cell of the medical image(s), output by a trained deep neural network, matches a target appearance classification. The trained deep neural network may map input medical images to one or more appearance classification cells of an appearance classification matrix based on display appearance characteristics of the medical image. Method 200 may be executed by one or more of the systems described above. In one embodiment, medical imaging system 100 may execute one or more operations of method 200 to select display settings of a medical image based on output of a deep neural network. In this way, a clinician may evaluate/diagnose medical images with a consistent presentation. Although the below description of method 200 emphasizes WW and WC, it will be appreciated that method 200 may be advantageously implemented to intelligently select display settings other than WW and WC, without departing from the scope of the current disclosure.

Method 200 begins at operation 202, where the medical imaging system acquires a medical image of an anatomical region of a patient. In some embodiments, operation 202 may include medical imaging device 140 acquiring one or more medical images of an anatomical region of interest from a patient. In one example, operation 202 may comprise a medical imaging device acquiring an x-ray image of a patient. Medical images may be acquired using one or more known imaging modalities, including MRI, PET, CT, x-ray, ultrasound, etc. Acquired medical images may comprise two-dimensional (2D) or three-dimensional (3D) images, and may include a single color channel, or a plurality of color channels. In some embodiments, acquired medical images may be transmitted to a remote image processing device. In some embodiments, the medical imaging system includes a built in image processing device.

At operation 204, the medical imaging system pre-processes the acquired medical image to produce a pre-processed medical image. In some embodiments, operation 204 includes the medical imaging system shuttering, cropping, and/or resizing the medical image. In some embodiments, the acquired medical image may be cropped or resized at operation 204 to fit a pre-determined format. In some embodiments, the pre-determined format comprises a format compatible with a trained deep neural network. In some embodiments, a trained deep neural network may comprise an input layer configured to receive image data from images of a pre-determined size, and operation 204 may comprise resizing the acquired medical image to match the pre-determined size. In some embodiments, operation 204 comprises the medical imaging system performing bilinear or bicubic interpolation to increase a size of an acquired medical image. In some embodiments, operation 204 comprises the medical imaging system pooling image data of the acquired medical image to decrease a size of the acquired medical image.

At operation 206, the medical imaging system applies a first WW and a first WC to the pre-processed medical image to produce a temporary display image. In some embodiments, initial values for the first WW and the first WC may be selected based on analysis of the pixel/voxel intensity histogram of the acquired medical image, and updated values of the first WW and the first WC may thereafter be determined based on an appearance classification cell output by the trained deep neural network of operation 208. In some embodiments, the medical imaging system may generate a first LUT based on the first WW and the first WC, and may apply the first LUT to each pixel/voxel of the pre-processed medical image to produce the temporary medical image, without altering the image data of the pre-processed medical image. In this way, image data of the medical image acquired at operation 202, may be preserved, while the temporary medical image may proceed to operation 208.

At operation 208, the medical imaging system maps the temporary display image to an appearance classification cell of an appearance classification matrix using a trained deep neural network. Operation 208 may include inputting image data from the temporary display image into an input layer of the trained deep neural network. The trained deep neural network may comprise one or more convolutional layers, wherein one or more features in the input medical image data may be identified by passing one or more learned filters across each sub-region of the temporary display image. The features identified/extracted in this manner include spatial contextual information of said features, as each extracted feature is associated with a particular sub-region in the temporary display image. Features output by shallower layers of the trained deep neural network may be received as input by deeper layers of the trained deep neural network, and thereby enable composite features (that is, features comprising spatial patterns of other features) to be extracted.

The trained deep neural network may comprise one or more activation functions, which may receive input(s) from a preceding layer, and may map the received inputs via a non-linear function to an output. Activation functions may comprise substantially any activation functions known in the art, such as rectified linear units (ReLU). The trained deep neural network may further include one or more pooling layers, such as maximum pooling layers, minimum pooling layers, average pooling layers, etc., wherein outputs from a plurality of neurons/feature channels of a preceding layer are received as input and an output of reduced dimension is produced. In one example, a pooling layer may receive four inputs, average each of the four inputs, and produce a single output equaling the average of the four inputs, thereby reducing a four-dimensional input vector into a one-dimensional output vector.

The trained deep neural network may include one or more fully connected layers (also referred to as dense layers), wherein each node/neuron of an $n^{th}$ layer is connected to every node of an $(n+1)^{th}$ layer, wherein n is a positive integer. In some embodiments, the convolutional layers (and optionally the pooling layers) may feed into one or more fully connected layers, wherein the fully connected layers may be configured as a classifier. The classifier may receive one or more features extracted from image data of the temporary display image by the subsequent convolutional layers, and may output a probability score for one or more appearance classification cells of an appearance classification matrix. Turning briefly to FIG. 8, an illustration of pairs of temporary display images and corresponding probability scores for appearance classification cells of an appearance classification matrix, output by a trained deep neural network, are shown.

Following operation 208, method 200 may proceed to operation 210. Operation 210 includes the medical imaging system evaluating if the appearance classification of the temporary display image matches a target appearance classification with greater than a threshold probability. The target appearance classification comprises a pre-determined appearance classification cell of the appearance classification matrix. In some embodiments, operation 210 comprises the medical imaging system comparing the appearance classification cell output by the trained deep neural network at operation 208, and determining if the output appearance classification cell equals the target appearance classification, and further, determining if a probability score associated with the output appearance classification cell is greater than a pre-determined threshold probability. In some embodiments, the probability threshold may be set at 0.80, and at operation 210, the appearance classification of the temporary medical image may be considered as matching the target appearance classification with greater than the threshold confidence if a probability score of the appearance classification is 80% or greater. If at operation 210 the medical imaging system determines that the appearance classification cell determined for the temporary medical image by the trained deep neural network matches the target appearance classification with greater than the threshold probability, method 200 proceeds to operation 214.

However, if at operation 210 the medical imaging system determines that the appearance classification cell does not match the target appearance classification with greater than the threshold probability, method 200 may proceed to operation 212. At operation 212, the medical imaging system updates the first WW and the first WC based on the appearance classification cell output at operation 208 before returning to operation 206. Thus, method 200 may repeat operations 206, 208, 210, and 212, until a first WW and a first WC are selected which produce a temporary display image that maps to an appearance classification cell matching the target appearance classification with greater than a threshold probability.

Turning briefly to FIG. 8, an illustration of one embodiment of the iterative process of determining display settings, such as described with regards to operations 206, 208, 210, and 212, is shown. In particular, FIG. 8 illustrates six iterations of display setting selection, first iteration 802, second iteration 804, third iteration 806, fourth iteration 808, fifth iteration 810, and sixth iteration 812. For each iteration, an associated temporary display image and appearance classification cell is shown. The appearance classification cells are shown within an appearance classification matrix, wherein a centermost appearance classification cell (the appearance classification cell in the $4^{th}$ row and the $4^{th}$ column), is a target appearance classification, towards which the appearance of the temporary display image converges through each of the six iterations. It will be appreciated that the current disclosure provides for more or less than six iterations.

In FIG. 8, the first iteration 802, and the second iteration 804, both show that the temporary medical image was mapped to a plurality of appearance classification cells. In embodiments where a temporary medical image is mapped to a plurality of appearance classification cells, wherein each appearance classification cell includes a probability score/confidence, parameters for updating the current WW and the current WC are determined for each of the plurality of appearance classification cells individually, and then a weighted average is computed for each of the parameters by weighting the parameters determined for each appearance classification cell by a corresponding probability/confidence score. In some embodiments, each appearance classification cell may include a WW scaling factor and a WC offset, relative to the target appearance classification cell, and upon mapping of a temporary medical image to a first appearance classification cell and a second appearance classification cell, a weighted average of a first WW scaling factor and a second WW scaling factor (corresponding to the first appearance classification and the second appearance classification, respectively) may be determined based on a first probability score and a second probability score (corresponding to the first appearance classification and the second appearance classification, respectively). Likewise, a weighted average WC offset may be determined for the temporary medical image by multiplying a first WC offset corresponding to the first appearance classification cell by the first probability score of the first appearance classification to produce a first weighted WC, multiplying a second WC offset corresponding to the second appearance classification cell by the second probability score of the second appearance classification to produce a second weighted WC, and adding first weighted WC with the second weighted WC to produce a weighted average WC, which may be used to update the current WC of the temporary medical image.

Returning to FIG. 2, at operation 210, responsive to a temporary display image being produced which has a display appearance matching a target appearance classification, method 200 may proceed to operation 214. At operation 214, the medical imaging system adjusts the first WW and the first WC based on pre-selected user preferences to produce a second WW and a second WC. In some embodiments, operation 214 includes the medical imaging system retrieving from a location in non-transitory memory, a file storing said pre-selected user display appearance preferences. In some embodiments, the user display appearance preferences comprise a set of mappings or transformations from average display settings of medical images matching the target appearance classification, to a set of user preferred display settings corresponding to a user preferred appearance. Operation 214 may further include automatically applying the retrieved mapping/transformation to the first WW and to the first WC, to produce the second WW and the second WC. In some embodiments, a user's display appearance preferences may include a WC offset and a WW scaling factor, wherein producing the second WC may comprise adding the WC offset to the first WC, and wherein producing the second WW may comprise multiplying the first WW by the WW scaling factor.

In some embodiments, a user may specify a preferred display appearance by manually adjusting display settings of a test image. In one example, a test image may be displayed to a user via a display device, wherein the display settings of the test image are the average display settings of medical images matching the target appearance classification. The user may manually adjust one or more of the display settings of the test image, until the test image matches a user's display appearance preferences. The adjustments made by the user to the display settings of the teste image, may be stored may be stored at the pre-determined location of non-transitory memory, for later access.

At operation 216, the medical imaging system applies the second WW and the second WC to the medical image acquired at operation 202 to produce a display image. In some embodiments, the medical imaging system may generate a second LUT based on the second WW and the second WC, and may apply the second LUT to each pixel/voxel of the medical image to produce the display image, without altering the image data of the medical image. In this way, image data of the medical image acquired at operation 202, may be preserved.

At operation 218, the medical imaging system displays the display image via a display device. In some embodiments, operation 218 may comprise displaying the display image produced at operation 216, via a display device, such as display device 120.

At operation 220, the medical imaging system optionally receives user input via a user input device, and further adjusts the second WW and the second WC of the display image based on the received user input to produce a third WW and a third WC. The third WW and the third WC may be applied to the display image to produce an updated display image. In some embodiments, the user input comprises a brightness selection and/or a contrast selection.

Turning briefly to FIG. 9, one embodiment of a GUI 900 for enabling a user to "fine tune" the display settings of a display image 904a, is shown. FIG. 9 shows GUI 900 before and after a user input is received. In particular, FIG. 9 shows display image 904a, and updated display image 904b, wherein the display settings of display image 904a are adjusted based on user repositioning of contrast slider 910 and brightness slider 912 to produce updated display image 904b. Both the contrast slider 910 and the brightness slider 912 include an indication of deviation from the display settings automatically selected according to one or more operations of method 200. As can be seen, prior to receiving user input, the contrast slider 910 and brightness slider 912 are both at a "default" or zero position, that is, the position of the contrast slider 910 and brightness slider 912 corresponds to the display settings automatically selected according to one or more operations of method 200. After user input is received, and the contrast slider 910 and brightness slider 912 are repositioned based on said user input, the contrast slider 910 and the brightness slider bar 912 are updated to indicate the extent of deviation from the initial slider positions. The indication of deviation from the automatically determined display settings may enable a user to more easily determine if, and by how much, display settings are adjusted from the automatically selected user settings, which, in some embodiments, may inform a user's to update pre-selected user preferences to more closely match a preferred display appearance, thereby reducing frequency of manual user adjustment of display settings, and expediting a user's workflow.

Following operation 220, method 200 may end. Method 200 may enable automatic selection of display settings for one or more medical images, wherein said display settings, when applied to the one or more medical images, may produce one or more corresponding display images having consistent display appearance. Method 200 may comprise selecting display settings for a medical image based on output of a deep neural network trained to classify medical images based on display appearance into one or more appearance classification cells of an appearance classification matrix. By mapping the medical image to the one or more appearance classification cells of the appearance classification matrix using the trained deep neural network, a more holistic assessment of the appearance of the medical image may be made.

Further, the trained deep neural network may classify an input medical image based on a plurality of learned image features, wherein said image features may comprise spatial intensity/color patterns. The trained deep neural network may implicitly extract position and orientation information of features present in the medical image, and may further identify/extract the relative spatial relationship between features present in the medical image. By classifying medical image display appearance based on the spatial configuration and types of features present within a medical image, as opposed to evaluating medical images based on pixel intensity histograms, appearance classifications may more closely approximate appearance classification of a human expert.

Further, as deep neural networks may learn to identify image features correlated with the appearance classification of a medical image, features which do not correlate with the appearance classification of medical images, such as image artifacts, including non-anatomical foreign bodies (e.g., surgical pins), may be ignored/attenuated. Thus, display settings selected based on an appearance classification determined using a trained deep neural network may be substantially less sensitive to noise and/or image artifacts than conventional approaches, as the trained deep neural network may differentiate between regions of a medical image comprising noise/image artifacts, and regions of the medical image comprising anatomical regions of interest. Further, the current approach does not rely on explicit segmentation and removal/masking of image artifacts prior to determination of display settings, thereby increasing computational efficiency and speed.

A technical effect of automatically selecting display settings for a medical image based on an appearance classification cell output by a trained deep neural network, wherein said appearance classification cell comprises a pre-determined difference/adjustment factor in one or more display settings relative to a target appearance classification, is that the display settings of the medical image may be iteratively updated based on said difference in the one or more display settings, to enable a display appearance of the medical image to converge to a pre-determined target appearance classification cell. Further, a technical effect of automatically determining medical image display appearance classifications based on the spatial configuration and types of features present within said medical images using a trained deep neural network, is that said appearance classifications may more closely approximate appearance classifications of a human expert, thereby enabling display setting adjustments to be made to the medical images to produce a plurality of medical images having a user's desired display appearance.

Turing to FIG. 3, an example of a method 300 for generating training data pairs, which may be used to train a deep neural network to classify medical images based on display appearance, is shown. Method 300 may be executed by one or more of the systems described herein. In one embodiment, method 300 may be executed by medical imaging system 100.

Method 300 begins at operation 302, where the medical imaging system selects a plurality of medical images. In some embodiments, operation 302 comprises selecting a plurality of medical images responsive to each of the plurality of medical images comprising image data of a pre-determined anatomical region. In one example, operation 302 may comprise the medical imaging device selecting a plurality of medical images of hands. In some embodiments, operation 302 may comprise the medical imaging device selecting a plurality of medical images of ribs. In some embodiments, operation 302 comprises the medical imaging system selecting a plurality of medical images based on an imaging modality used to acquire said plurality of medical images. In some embodiments, operation 302 comprises the medical imaging system selecting a plurality of medical images of a single type of imaging modality. The medical imaging system may select the plurality of medical images based on one or more pieces of metadata associated therewith. In some examples, operation 302 comprises selecting anonymized medical images, wherein personally identifying information has been scrubbed from the medical images. In some embodiments, the medical images selected at operation 302 may be divided into a first portion, a second portion, and a third portion, wherein the first portion may be used to train a deep neural network, the second portion may be used to validate the deep neural network (for use in adjusting hyper-parameters of the deep neural network), and the third portion may be used to test performance of the deep neural network post training.

At operation 304, the medical imaging system adjusts the WW and WC of each of the plurality of medical images, to produce a plurality of appearance normalized medical images. As used herein, appearance normalized medical images are medical images having similar, or the same, overall display appearance (e.g., anatomical feature brightness relative to background brightness, tissue contrast, edge definition, noise etc.).

In some embodiments, the medical imaging system adjusts the WW and WC of each of the plurality of medical images based on input received via a user input device. In some embodiments, a human expert may input WW and WC settings to the medical imaging system using a user input device, to bring a display appearance of each of the plurality of medical images into uniformity. The WW and WC settings which produce consistent display appearance may differ. As an example, a first medical image may match a user preferred display appearance when a first set of display settings are applied, whereas a second medical image may match the same user preferred display appearance with a second, different, set of display settings applied.

At operation 306, the medical imaging system determines an average WW and an average WC for the plurality of appearance normalized medical images. In some embodiments, operation 306 includes the medical imaging system accessing each of the plurality of WWs and WCs determined at operation 304, and determining an average WW and an average WC based thereon. The average WW and the average WC may be representative of a target appearance classification.

At operation 308, the medical imaging system automatically generates an appearance classification matrix comprising a plurality of appearance classification cells, based on the average WW and the average WC of the target appearance classification. In some embodiments, the appearance classification matrix may comprise an N-by-N grid of cells (where N is an integer greater than 1), herein referred to as appearance classification cells, wherein each of the appearance classification cells corresponds to a distinct display appearance class label. In some embodiments, N may consist of odd integers greater than 1. In some embodiments, the appearance classification matrix may comprise a 7-by-7 matrix. In other words, the appearance classification matrix comprises a plurality of display appearance classification cells, arranged in a matrix, with each distinct cell within the matrix corresponding to a distinct display appearance label.

In some embodiments, the plurality of appearance normalized images produced at operation 304, may correspond to a centermost cell of the appearance classification matrix, said centermost cell may also be referred to as a target appearance classification matrix. Said centermost cell may be associated with the average WW and the average WC determined at operation 304. Each remaining cell of the appearance classification matrix (that is, each appearance classification cell other than the centermost cell corresponding to the target appearance classification) may be uniquely addressed by a distinct WW and WC determined based on the position of each cell with respect to the centermost cell, and further based on the average WW and the average WC. In some embodiments, each row of the appearance classification matrix may have an associated WW scaling factor, and each column of the appearance classification matrix may have an associated WC offset, wherein the WW for each cell of a particular row is determined by multiplying the WW scaling factor associated with the row by the average WW, and wherein the WC for a particular column is determined by adding the WC offset to the average WC. The WW scaling factor of the centermost row may be 1.0, while a WC offset of the centermost column may be 0.

Turning briefly to FIG. 5, an illustration of the gradations in display settings throughout the rows and columns of an appearance classification matrix is shown. FIG. 5 comprises a plurality of display images 500, arranged in a 7-by-7 grid, corresponding to a 7-by-7 appearance classification matrix. Each display image of the plurality of display images 500 possesses the display settings associated with a corresponding appearance classification cell of a 7-by-7 appearance classification matrix. In other words, a display image at the top left of FIG. 5 possesses a WW and a WC corresponding to the WW and WC of the top left cell of a 7-by-7 appearance classification matrix.

At operation 310, the medical imaging system augments the plurality of appearance normalized medical images to generate a plurality of augmented medical images. In some embodiments, in order to increase a size of a training data pool, the medical imaging system may alter one or more properties of the plurality of appearance normalized medical images by rotating, flipping and/or cropping one or more of the plurality of appearance normalized medical images. In some examples, for each appearance normalized medical image, 10 to 15 augmented medical images (and any integer number there between) may be generated.

At operation 312, the medical imaging system pairs each of the plurality of augmented medical images with an appearance classification cell of the appearance classification matrix. In some embodiments, operation 312 may comprise the medical imaging system generating a random or pseudo-random number, and selecting one of the plurality of appearance classification cells based on said random or pseudo-random number to pair with an augmented medical image.

At operation 314, the medical imaging system produces a plurality of training images by adjusting the WW and the WC of each of the plurality of augmented medical images based on a paired appearance classification cell. As each appearance classification cell comprises a unique combination of WW and WC, operation 314 may comprise accessing the WW and WC of an appearance classification cell paired with an augmented medical image, and generating a LUT based on said WW and WC, and applying the LUT to the augmented medical image to produce a training image having display appearance corresponding to the appearance classification cell.

At operation 316, the medical imaging system stores each training image and paired appearance classification cell as a training data pair. Following operation 316, method 300 may end. As used herein, an appearance classification cell paired with a training image having a display appearance matching the appearance classification cell, may also be referred to as a ground truth appearance classification cell.

Figure 4:
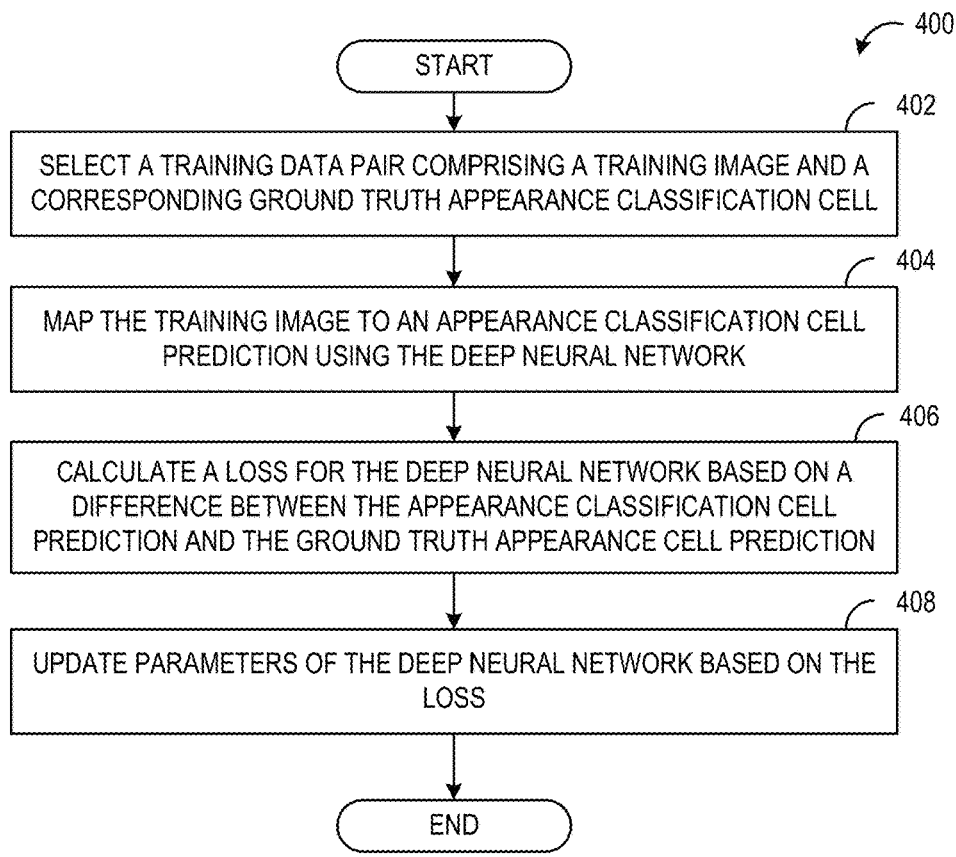
FIG. 4 shows a flowchart of an exemplary method for training a deep neural network to map medical images to one or more appearance classification cells of an appearance classification matrix using a plurality of training data pairs.

Turning to FIG. 4, an example of a training method 400, which may be executed by one or more of the systems described above, is shown. In one embodiment, method 400 may be used to train a deep neural network to classify medical images into one or more appearance classification cells of an appearance classification matrix using training data pairs generated by execution of one or more operations of method 300.

Method 400 begins at operation 402, where an image processing device selects a training data pair comprising a training image and a corresponding ground truth appearance classification cell, from a location in non-transitory memory. In some embodiments, the image processing device may select a training data pair based on one or more pieces of metadata associated with said training data pair. In some embodiments, the image processing device may select a training data pair responsive to the training data pair including a training image of a pre-determined anatomical region, thereby enabling a deep neural network to be selectively trained to classify display appearance of said pre-determined anatomical region. In some embodiments, the image processing device may select a training data pair responsive to said training data pair including a particular ground truth appearance classification cell, wherein said particular ground truth appearance classification cell may be determined by the image processing device according to an appearance cell classification distribution. In one embodiment, the appearance cell classification distribution may be an even or equal distribution, wherein training data pairs comprising ground truth appearance classification cells are selected at an equal sampling rate from each of a plurality of appearance classification cells of an appearance classification matrix.

At operation 404, the image processing device maps the training image to an appearance classification cell prediction using a deep neural network. In some embodiments, operation 404 comprises inputting image data of the training image into an input layer of the deep neural network and receiving output from an output layer of the deep neural network, wherein the output comprises the appearance classification cell prediction. The deep neural network may comprise an input layer configured to receive image data, one or more convolutional layers configured to extract visual features from the image data, one or more fully connected layers configured to receive extracted features from the one or more convolutional layers and produce based thereon a classification of the input image data, and an output layer configured to output said classification of the input image data in a pre-determined format. Convolutional layers of the deep neural network may comprise one or more filters, which in turn may comprise a plurality of weights configured in a particular spatial orientation. Said filters may identify/extract patterns present in input image data. In some embodiments, the deep neural network may comprise a ResNet architecture of substantially any number of layers. In one embodiment, the deep neural network may comprise a ResNet50.

Output of the deep neural network, may comprise a probability score for one or more appearance classification cells of an appearance classification matrix. Briefly, an appearance classification matrix may comprise an N-by-N grid (or matrix) of appearance classification cells (wherein N is an integer greater than 1), and output of the deep neural network may comprise an N-by-N grid of probability scores, wherein each of the N-by-N probability scores indicates a probability of the input medical image's display appearance matching a corresponding appearance classification cell of the N-by-N appearance classification matrix.

At operation 406, the image processing device calculates a loss for the deep neural network based on a difference between the appearance classification cell prediction and the ground truth appearance cell. In some embodiments, the image processing device may calculate the loss using loss a function. In some embodiments, the loss may comprise a categorical cross entropy. In some embodiments, a ground truth appearance classification cell comprises a probability of 1.0 for a single appearance classification cell of the appearance classification matrix, and the appearance classification cell prediction of the deep neural network comprises one or more probability scores for one or more of the appearance classification cells of the appearance classification matrix. In some embodiments, operation 406 includes the image processing device performing a cell-wise subtraction of the ground truth appearance classification cell from the one or more probability scores of the appearance classification cell prediction to produce a plurality of cell-wise differences, and inputting the plurality of cell-wise differences into a loss function.

At operation 408, the image processing device updates parameters of the deep neural network based on the loss. In some embodiments, updating parameters of the deep neural network includes backpropagating the loss through the layers of the deep neural network using a backpropagation algorithm. In one embodiment, operation 408 comprises the image processing device adjusting the weights and biases of the layers of the deep neural network based on the loss determined at operation 406. In some embodiments, back propagation of the loss may occur according to a gradient descent algorithm, wherein a gradient of the loss function (a first derivative, or approximation of the first derivative) is determined for each weight and bias of each layer of the deep neural network. Each weight (and bias) of the deep neural network may be updated by adding the negative of the product of the gradient of the loss, determined with respect to the weight (or bias) and a predetermined step size, according to the below equation:

$$P_{i+1} = P_i - \eta \frac{\partial Loss}{\partial P_i}$$

where $P_{i+1}$ is the updated parameter value, $P_i$ is the previous parameter value, $\eta$ is the step size, and $$\frac{\partial Loss}{\partial P_i}$$

is the partial derivative of the cumulative loss with respect to the previous parameter.

Following operation 408, method 400 may end. It will be appreciated that method 400 may be repeated until one or more conditions are met. In some embodiments, the one or more conditions may include the weights and biases of the deep neural network converging (that is, a rate of change of the parameters decreases to below a pre-determined threshold rate of change), the loss determined at operation 406 decreasing to below a pre-determined, non-zero, loss threshold. In this way, method 400 enables a deep neural network to learn a mapping from medical images to appearance classification cells.

Turning to FIG. 6, a first plurality of medical images 602, having display settings selected according to a conventional approach, and a second plurality of medical images 604, comprising the same medical images as the first plurality of medical images 602, but with display settings determined according an exemplary embodiment of the current disclosure, are shown. Each row of both first plurality of medical images 602 and second plurality of medical images 604 corresponds to a distinct anatomical region, e.g., the first row shows images of vertebrae, the second row shows images of ankles, the third row shows images of feet, the fourth row shows images of hands, and the fifth row shows images of ribs. Differences in display appearance are readily apparent between medical images of a same row (a same anatomical type) in first plurality of medical images 602, whereas display appearance (e.g., brightness and contrast) is consistent within each row of second plurality of medical images 604.

Similarly, turning to FIG. 7, a first plurality of x-ray images 702 of a hand of a patient, and a second plurality of x-ray images 704 of a hand of a patient, are shown. Display settings of the first plurality of medical images 702 comprise display settings selected based on pixel intensity histograms of the first plurality of x-ray images, whereas the display settings of the second plurality of x-ray images 704 comprise display settings selected based on output of a trained deep neural network, where in some embodiments, said output comprises one or more appearance classification cells of an appearance classification matrix.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method comprising:
   generating an appearance classification matrix;
   generating a plurality of training data pairs using the appearance classification matrix, wherein the plurality of training data pairs comprise a plurality of training images and a plurality of ground truth appearance classification cells corresponding to the plurality of training images;
   training a deep neural network using the plurality of training data pairs to produce a trained deep neural network;
   receiving a medical image;
   mapping the medical image to an appearance classification cell of the appearance classification matrix using the trained deep neural network;
   selecting a first window-width (WW) and a first window-center (WC) for the medical image based on the appearance classification and a target appearance classification;
   adjusting the first WW and the first WC based on user preferences to produce a second WW and a second WC; and
   displaying the medical image with the second WW and the second WC via a display device;
   wherein generating the appearance classification matrix comprises:
      receiving a plurality of medical images;
      adjusting a first plurality of WWs and a first plurality of WCs of the plurality of medical images to produce a first plurality of appearance normalized medical images;
      averaging the first plurality of WWs to produce an average WW;
      averaging the first plurality of WCs to produce an average WC;
      assigning the average WW and the average WC to the target appearance classification of the appearance classification matrix; and
      generating a plurality of appearance classification cells around the target appearance classification based on the average WW and the average WC.

2. The method of claim 1, wherein generating the plurality of training data pairs using the appearance classification matrix comprises:
   selecting an image;
   pairing the image to a ground truth appearance classification cell of the appearance classification matrix;
   adjusting a WW and a WC of the image based on the ground truth appearance classification cell to produce a training image matching appearance characteristics of the ground truth appearance classification cell; and storing the training image and the ground truth appearance classification cell corresponding to the training image as a training data pair in non-transitory memory.

3. The method of claim 1, wherein selecting the first WW and the first WC for the medical image based on the appearance classification and the target appearance classification comprises iteratively selecting WW values and WC values until the appearance classification of the medical image matches the target appearance classification.

4. The method of claim 1, wherein the appearance classification cell includes a WW difference between the appearance classification cell and the target appearance classification, and wherein the appearance classification cell further includes a WC difference between the appearance classification cell and the target appearance classification.

5. The method of claim 4, wherein selecting the first WW and the first WC for the medical image based on the appearance classification and the target appearance classification comprises:

selecting the first WW based on the WW difference; and
selecting the first WC based on the WC difference.

6. A method comprising:

generating an appearance classification matrix;

generating a plurality of training data pairs using the appearance classification matrix, wherein the plurality of training data pairs comprise a plurality of training images and a plurality of ground truth appearance classification cells corresponding to the plurality of training images;

training a deep neural network using the plurality of training data pairs to produce a trained deep neural network;

receiving a medical image;

mapping the medical image to an appearance classification cell of the appearance classification matrix using the trained deep neural network;

selecting a first window-width (WW) and a first window-center (WC) for the medical image based on the appearance classification and a target appearance classification;

adjusting the first WW and the first WC based on user preferences to produce a second WW and a second WC; and displaying the medical image with the second WW and the second WC via a display device;

wherein generating the plurality of appearance classification cells around the target appearance classification based on the average WW and the average WC comprises:

determining a position of a first appearance classification cell relative to the target appearance classification;

adjusting the average WW based on the position to produce a first appearance classification WW; and adjusting the average WC based on the position to produce a first appearance classification WC.

7. The method of claim 6, wherein generating the plurality of training data pairs using the appearance classification matrix comprises:

selecting an image;

pairing the image to a ground truth appearance classification cell of the appearance classification matrix;

adjusting a WW and a WC of the image based on the ground truth appearance classification cell to produce a training image matching appearance characteristics of the ground truth appearance classification cell; and storing the training image and the ground truth appearance classification cell corresponding to the training image as a training data pair in non-transitory memory.

8. The method of claim 6, wherein selecting the first WW and the first WC for the medical image based on the appearance classification and the target appearance classification comprises iteratively selecting WW values and WC values until the appearance classification of the medical image matches the target appearance classification.

9. The method of claim 6, wherein the appearance classification cell includes a WW difference between the appearance classification cell and the target appearance classification, and wherein the appearance classification cell further includes a WC difference between the appearance classification cell and the target appearance classification.

10. The method of claim 9, wherein selecting the first WW and the first WC for the medical image based on the appearance classification and the target appearance classification comprises:

selecting the first WW based on the WW difference; and
selecting the first WC based on the WC difference.

* * * * *